United States Patent [19]

Rio et al.

[11] Patent Number: 5,524,291
[45] Date of Patent: Jun. 11, 1996

[54] SUN VISOR FOR EYE GLASSES

[76] Inventors: Douglas A. Rio, 33 W. 460 Shagbark, Wayne, Ill. 60184; Charles E. Lab, 26001 W. Canal Rd., Minooka, Ill. 60447

[21] Appl. No.: 366,649

[22] Filed: Dec. 30, 1994

[51] Int. Cl.$^6$ ........................................................ A61F 9/04
[52] U.S. Cl. ........................................................ 2/13; 2/909
[58] Field of Search .................................. 2/13, 12, 909, 2/918, 209.12, 209.13, 10; 351/158

[56] References Cited

U.S. PATENT DOCUMENTS

| | | | |
|---|---|---|---|
| 2,544,221 | 3/1951 | Creighton | 2/13 |
| 4,293,958 | 10/1981 | Zauner | 2/12 |
| 4,393,519 | 7/1983 | Nicastro | 2/909 X |
| 4,547,903 | 10/1985 | Brown | 2/12 |
| 4,606,453 | 8/1986 | Burns | 2/13 X |

*Primary Examiner*—Peter Nerbun
*Attorney, Agent, or Firm*—Ernest Kettelson

[57] ABSTRACT

A sun visor for eye glasses, comprising a U-shape or arcuate frame member which supports a stretchable fabric covering, in which the fabric covering includes an upper and lower panel to provide a pocket therebetween. The upper and lower panels are sewn together around the arcuate or U-shape portion of their periphery in a pair of spaced apart peripheral seams that provides a peripheral through passageway for the U-shaped or arcuate frame member. The opposite end portions of the arcuate frame member project outwardly from each opposite opening to the peripheral through passageway. A strip of material having tiny hook members thereon is secured to the inwardly facing surface of each outwardly projecting end portion for releasably connecting to corresponding members having tiny loops thereon secured to the forward ends of the temple pieces of the eye glasses, to releasably secure the sun visor to the eye glasses. A relatively stiff but flexible supporting strip is secured to the laterally extending edge of the lower fabric panel, slightly longer than such edge whereby the strip has to be bowed slightly in the upward direction which in turn biases the laterally extending edge of the lower panel against the laterally extending edge of the upper panel, thereby biasing the entrance to the pocket towards the closed position. A retaining flap extends inwardly of the pocket from the laterally extending edge of the upper panel.

18 Claims, 6 Drawing Sheets

SUN VISOR FOR EYE GLASSES

BACKGROUND OF THE INVENTION

This invention relates to the field of sun visors, and particularly a sun visor which can be releasably secured to a pair of sunglasses or other types of eye glasses.

Prior art sun visors are typically a permanent part of another item such as the bill portion of a cap, or if they are separate items they include such things as an elastic band which goes around the wearer's head to hold a visor in place above the wearer's eyes.

The present invention is an improvement over the prior art in that it provides a sun visor which can be readily secured to a pair of sunglasses, or other eye glasses, held in place thereon above the lens of the eye glasses, and supported to extend outwardly therefrom. When through using the sun visor it can be readily disconnected from the eye glasses.

The sun visor in accordance with this invention also includes a storage pocket for items such as keys, a money clip, and even for the eye glasses themselves.

SUMMARY OF THE INVENTION

The sun visor in accordance with the present invention comprises a generally U-shaped or semi-circular peripheral frame member which supports and is covered by a stretchable fabric covering. This peripheral frame is small and lightweight, rigid enough to support the sun visor but flexible enough to be bent into its U-shaped or semi-circular configuration. The fabric covering of the visor comprises an upper panel and a lower panel of stretchable fabric material, each of generally U-shaped or semi-circular peripheral configuration, and each having a laterally extending straight edge extending across between the opposite free ends of the U-shape configuration.

The upper and lower fabric panels are sewn together around their peripheral U-shaped or semi-circular edges in an outer U-shaped peripheral seam, and again in an inner U-shaped peripheral seam spaced apart from the outer peripheral seam a sufficient short distance to provide a peripheral through passageway for the U-shaped peripheral frame member to be received in and threaded through.

The opposite free ends of the frame member project outwardly from each opposite opening to the peripheral through passageway a short distance of about a half inch. A strip of tiny hook connecting material, such as Velcro, is secured to the inwardly facing surface of such outward projections for releasable connecting engagement with corresponding strips of tiny loop connecting material supported at the forward ends of each opposite temple piece of the eye glasses adjacent its hinged connection to the lens supporting frame.

The upper and lower fabric panels which are supported by the U-shaped peripheral frame member are not sewn together along their laterally extending edges which extend across between the legs of the U-shaped frame member, and which lie adjacent to and slightly above the upper edge of the lens supporting frame of the eye glasses when in place thereon. The upper and lower fabric panels form a storage pocket for items such as keys, money clip, even the eye glasses themselves. The unsewn laterally extending edges of the upper and lower panels provide an entrance into the pocket.

A retaining flap extends inwardly of the pocket from the laterally extending edge of the upper fabric panel to help prevent items in the storage pocket from falling out inadvertently. A laterally extending support strip is secured along the inner surface of the laterally extending edge of the lower fabric panel. This support strip is about a half inch wide and about a half inch longer than the lineal dimension across the laterally extending edge of the lower fabric panel. This supporting strip is relatively stiff but can be flexed to bow in a slight arc by pressing the outer ends toward each other slightly. Since it is about a half inch longer than the lineal dimension across the laterally extending edge of the fabric panels, which corresponds in turn to the lineal dimension across the lens supporting frame of the eye glasses, namely about five and a half inches, the ends of the lateral supporting strip have to be pressed toward each other slightly to fit within the outer edges of the pocket and opposite edges of the U-shaped peripheral frame member. This causes the lateral supporting strip to bow slightly in the upward direction whereby the laterally extending edge of the lower panel becomes biased against the laterally extending edge of the upper panel. The entrance to the pocket is thus biased toward a closed position, which aids the inwardly projecting retaining flap of the upper panel in keeping items within the pocket from inadvertently falling out.

This slight bow upwardly also positions the laterally extending edges of the upper and lower panels along and slightly above the upper edge of the eye glass lens frame when the visor in accordance with this invention is releasably secured thereto.

Other improvements and advantages will become apparent from the more detailed description which follows, and from examining the accompanying drawings.

DESCRIPTION OF PREFERRED EMBODIMENT

Figure 1:
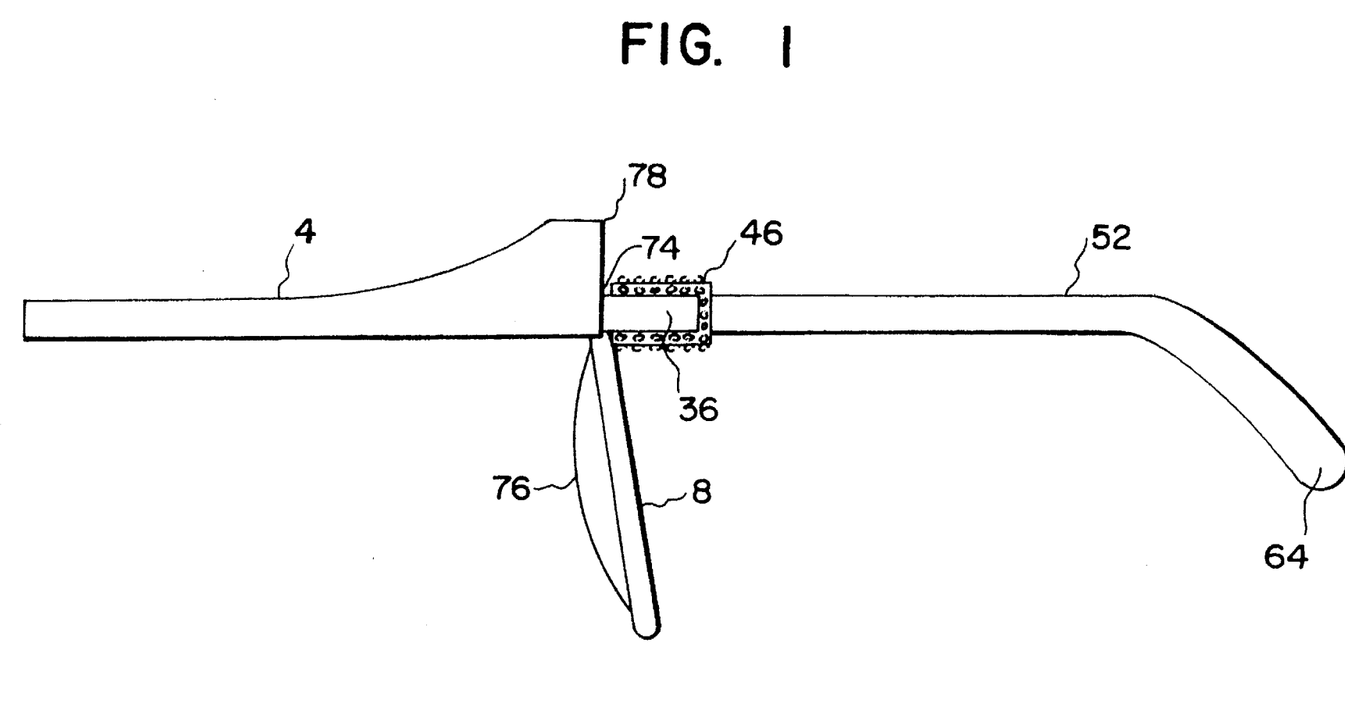
FIG. 1 is a side elevation view of a pair of sun glasses having a sun visor in accordance with this invention releasably secured thereon.
Figure 5:
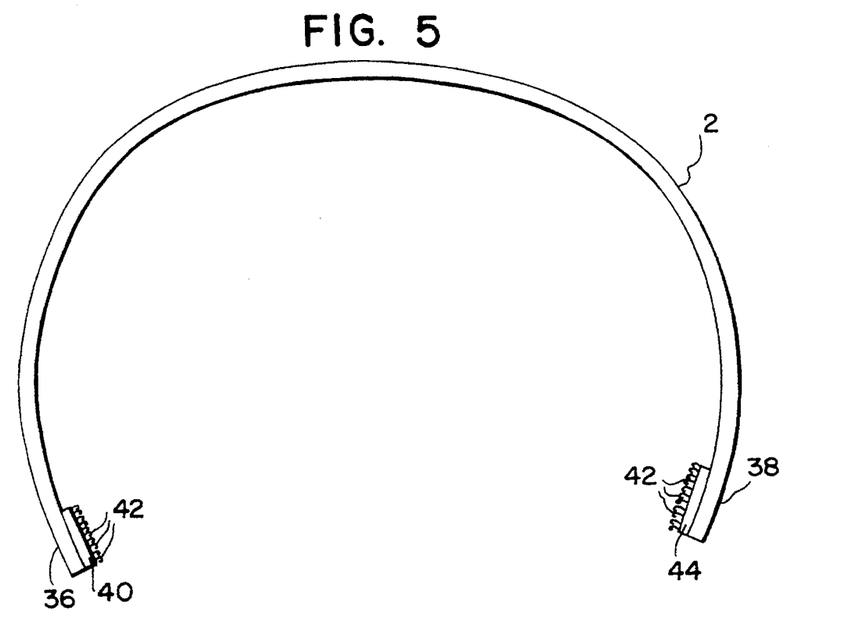
FIG. 5 is a plan view of the flexible frame member which supports the fabric covering.

A sun visor for use with eye glasses, and sun glasses in particular, in accordance with the present invention includes a flexible frame member 2 bent into a U-shaped configuration and a stretchable opaque fabric covering 4 supported on the frame member 2.

Figure 3:
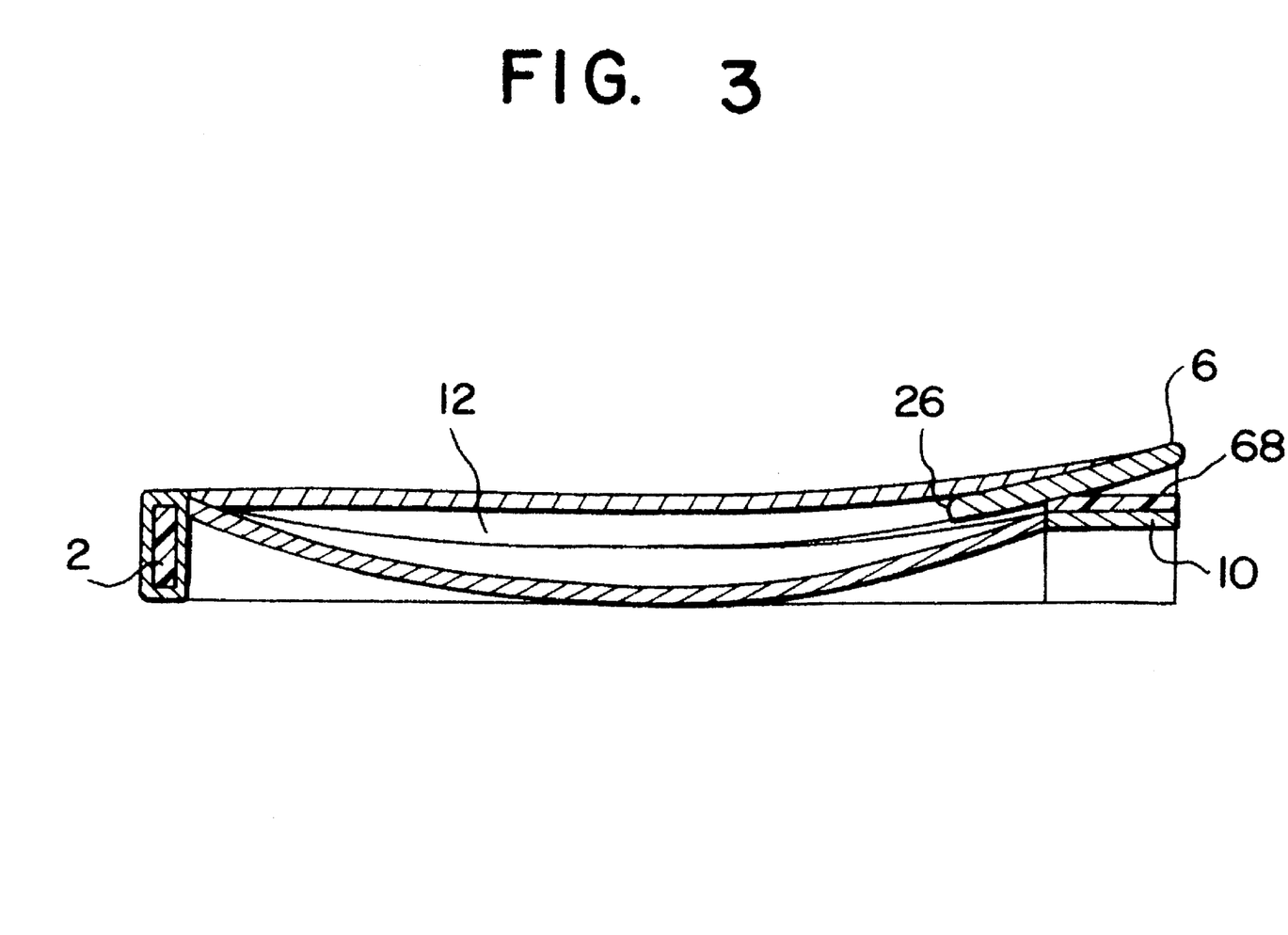
FIG. 3 is a section view taken on line 3—3 of FIG. 2.

The opaque fabric covering 4 comprises an upper panel 6 of flexible sheet material facing upwardly when in use secured to a pair of sun glasses 8 and a lower panel 10 of such material facing downwardly when so in use. The upper panel 6 and lower panel 10 form a pocket 12 having an entrance 14 facing rearwardly toward the sun glasses 8 when secured thereto.

Figure 4:
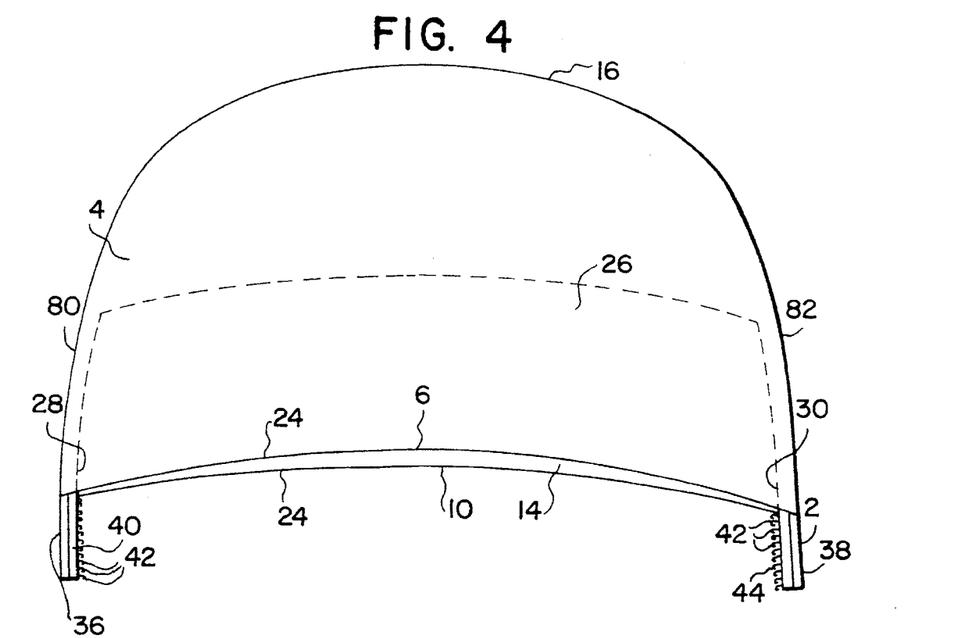
FIG. 4 is a top plan view of the sun visor in accordance with this invention, in which the inwardly projecting retaining flap of the upper fabric panel is shown within the pocket and in broken lines.
Figure 8:
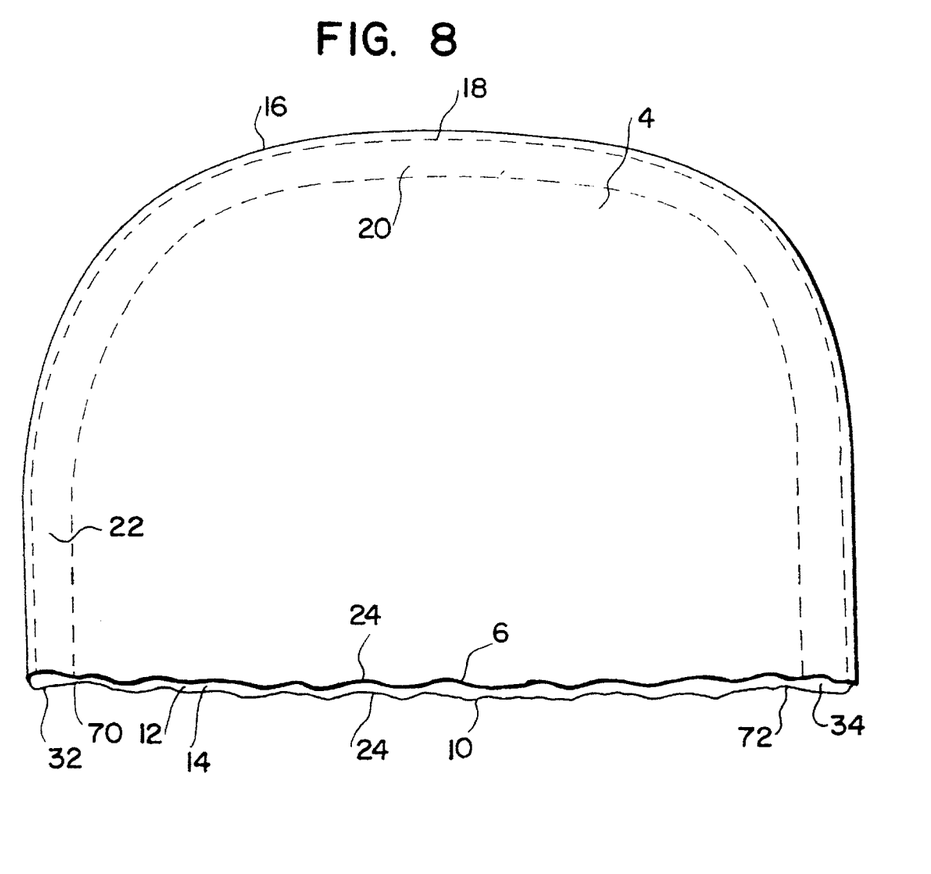
FIG. 8 is a top plan view of the fabric covering without the flexible frame member in place, to illustrate the outer and inner spaced apart peripheral seams which form the peripheral through passageway in which the supporting flexible frame member is received.

The upper and lower panels of sheet material 6 and 10 may be made from the same sheet of fabric, each cut into a generally U-shaped or semi-circular peripheral configuration. The peripheral U-shaped or semi-circular edges 16 of the upper panel 6 and lower panel 10 are sewn together in an outer peripheral seam 18. They are also sewn together along an inner peripheral seam 20 spaced apart inwardly a relatively short distance from the outer peripheral seam 18 to provide a peripheral through passageway 22 to receive the flexible frame member 2 therethrough. The laterally extending edges 24 of the upper panel 6 and lower panel 10 which border the entrance 14 to pocket 12 are not sewn together. Instead the edge 24 of the upper panel 10 is folded back to extend inwardly of the pocket 12 to provide a retaining flap 26. When an item or items such as credit cards, keys, or the glasses themselves are placed in the pocket 12, the retaining flap 26 serves to keep such items from falling back out. The outer edges 28 and 30 of the retaining flap 26 are sewn to the edges of the panels of sheet material.

In a preferred embodiment, the flexible frame member 2 has a width of about three-sixteenths of an inch and a thickness or cross-sectional dimension of about six-hundredths of an inch. A suitable material for the flexible frame member 2 is strip styrene.

To receive a flexible frame member 2 of such dimensions, the inner peripheral seam 20 of the fabric covering 4 is spaced apart inwardly from the outer peripheral seam 18 about one-quarter of an inch. That provides a peripheral through passageway 22 having a large enough cross-sectional dimension to receive a flexible frame member 2 which is three-sixteenths of an inch wide and six-hundredths of an inch thick.

The flexible frame member 2 has a linear dimension which is preferably about twelve to thirteen inches. The fabric covering 4 is preferably about five and a half to six inches across along its laterally extending edges 24, which corresponds generally with the width of sun glasses and other eye glasses with which the sun visor in accordance with this invention may be used.

Figure 2:
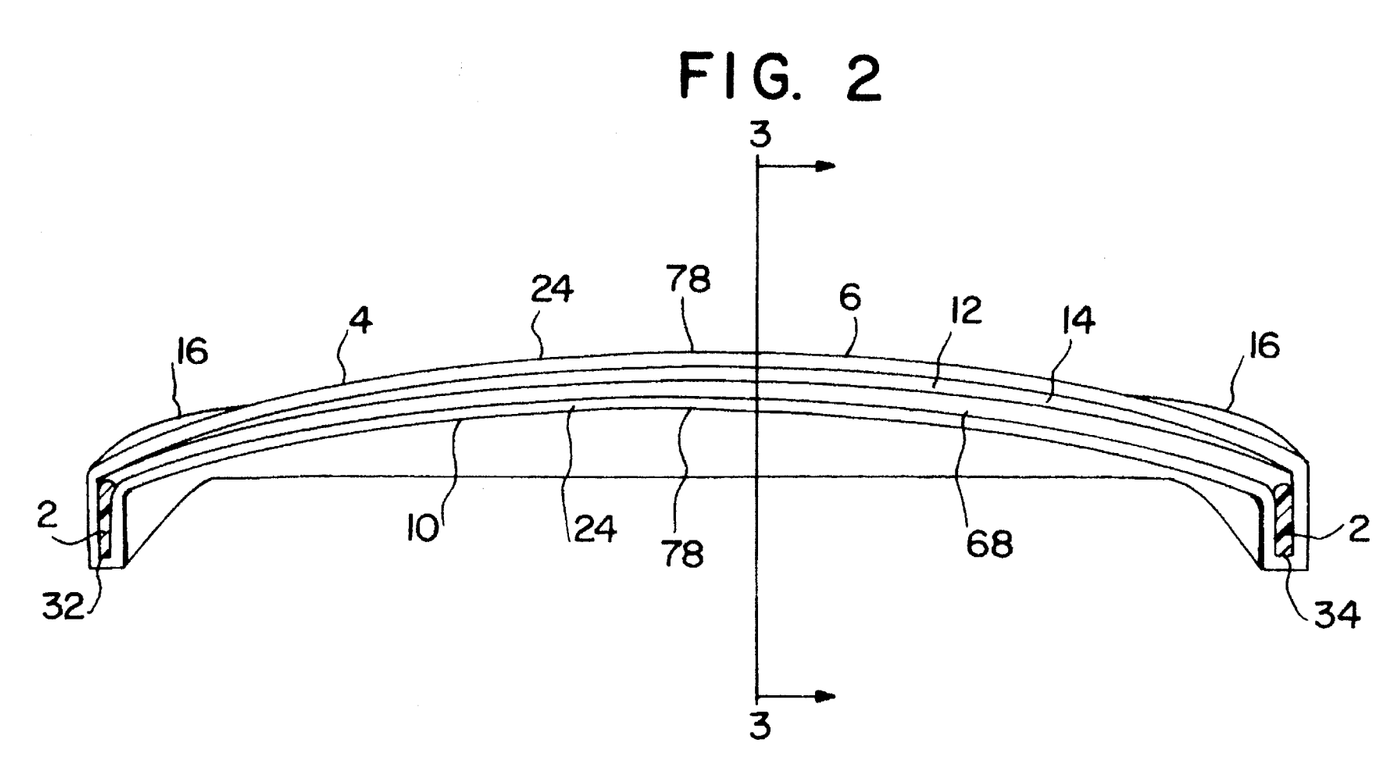
FIG. 2 is an end elevation view from the rear and looking forward of the sun visor in accordance with this invention, with the projecting connecting strips of the peripheral band cut off at the entrances to the peripheral through passageway on each opposite side to illustrate the entrance openings, the opposite ends of the peripheral band which is in the peripheral through passageway shown in section.

The peripheral through passageway 22 around the outer edge of the fabric covering 4 has a linear dimension of about eleven to twelve inches, in other words about an inch less than the linear dimension of the flexible frame member 2. The flexible frame member 2 thus extends outwardly from each opposite entrance or end 32 and 34 of the passageway 22 about one-half inch when received therein, to provide a first connecting strip 36 of the flexible frame member 2 projecting outwardly from end 32 of the fabric covering passageway 22 and a second connecting strip 38 thereof projecting outwardly from end 34 of the passageway 22.

A first visor retaining piece 40 having a plurality of tiny hook members 42 projecting outwardly therefrom is secured to the first connecting strip 36 of the flexible frame member 2. A second visor retaining piece 44 having a similar plurality of tiny hook members 42 projecting outwardly therefrom is secured to the second connecting strip 38.

Figure 6:
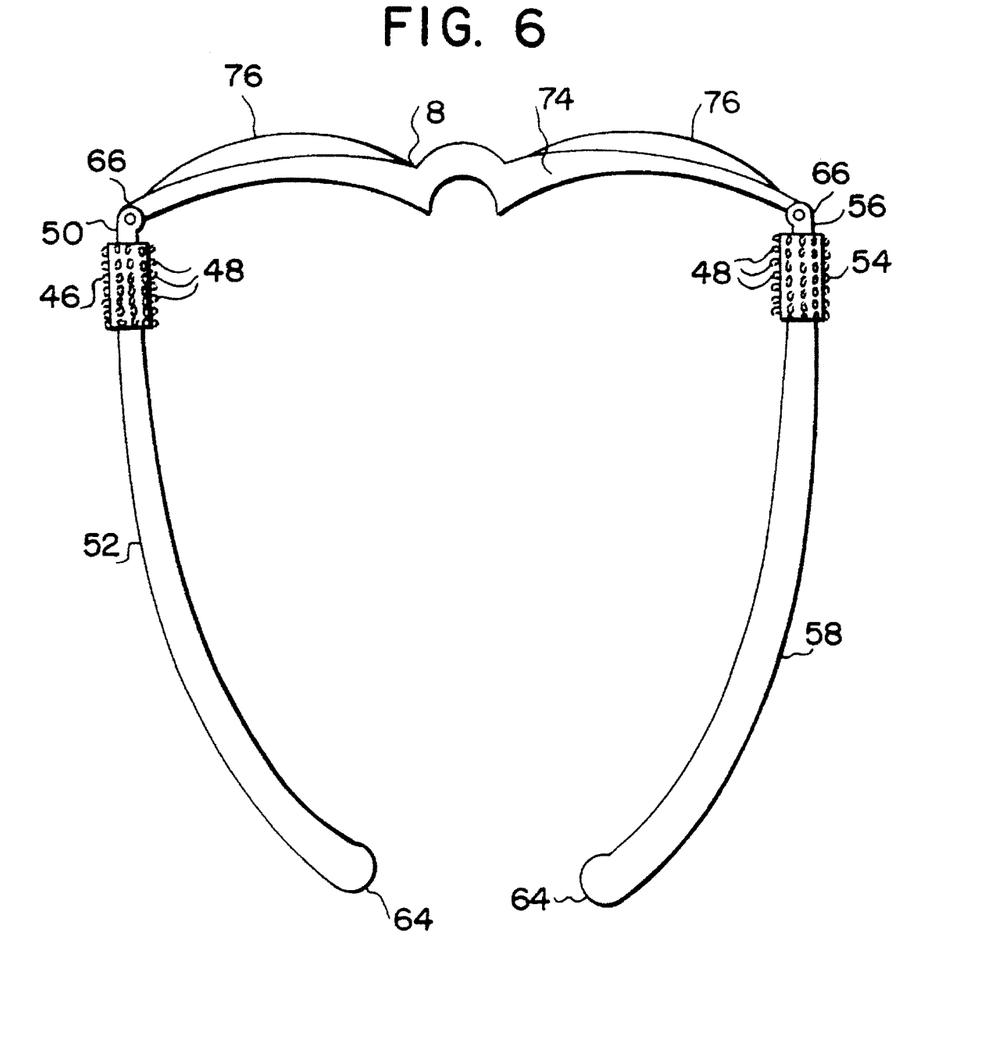
FIG. 6 is a top plan view of a pair of sun glasses showing the cooperative retaining members on the forward end of each of the temple pieces.

A first eyeglass cooperative retaining member 46 having a plurality of tiny loop members 48 projecting outwardly therefrom is secured to the forward end 50 of the first elongated temple piece 52 on one side of the sun glasses 8. A second eyeglass cooperative retaining member 54 having a plurality of tiny loop members 48 projecting outwardly therefrom is secured to the forward end 56 of the second elongated temple piece 58 on the other side of the sun glasses 8.

The visor retaining pieces 40 and 44 are preferably about one-half inch in length, and are secured to the inwardly facing side of the connecting strips 36 and 38 of the flexible frame member 2. The cooperative retaining members 46 and 54 secured to the forward ends of the temple pieces 52 and 58 are also preferably about one half inch in length. When the sun visor in accordance with this invention is placed in position to be secured to the sun glasses 8, the visor retaining pieces 40 and 44 of the visor span the respective cooperative retaining members 46 and 54 of the sun glasses 8 throughout their respective lengths of about one half inch. The visor retaining pieces 40 and 44 having the outwardly projecting tiny hook members 42 are pressed into contact with their respective cooperative retaining members 46 and 54 having the outwardly projecting tiny loop members 48 whereupon the hook members 42 releasably connect with and interengage with the loop members 48.

Figure 7:
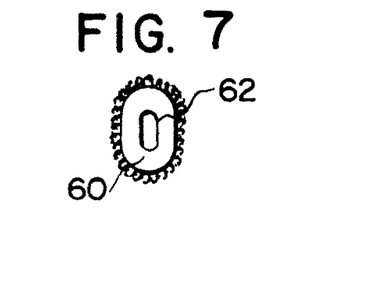
FIG. 7 is an end elevation view of one of the cooperative retaining members which are shown in FIG. 6 in place at the forward end of the temple pieces.

The eyeglass cooperative retaining members 46 and 54 as shown and described herein comprise an elongated flexible sleeve 60 about one-half inch in length having the tiny loop members 48 projecting outwardly around the entire outer surface of the sleeve 60 throughout its entire length. A bore 62 extends through the flexible sleeve 60, providing a through passageway to receive respective ones of the elongated temple pieces 56 and 58. The retaining members 46 and 54 are positioned to receive the rearward ends 64 of the temple pieces and then pushed forward thereon until they reach the forward ends abutting against the hinges 66 which connect the temple pieces to the sun glasses 8. The bore 62 of the eyeglass cooperative retaining members 46 and 54 has a cross-sectional dimension which corresponds to the cross-sectional dimension of the temple pieces 52 and 58. The flexible sleeve 60 of the eyeglass cooperative retaining members 46 and 54 is expandable and contractable whereby the bore 62 is sufficiently expandable to snugly receive the elongated temple pieces 52 and 58 therethrough and to hold the retaining members 46 and 54 in position thereon and against unintended longitudinal movement relative thereto until sufficient intended force is applied.

The tiny hook members 42 may of course be provided on the eyeglass cooperative retaining members 46 and 54, and the tiny loop members 48 on the visor retaining clips 40 and 44.

Figure 9:
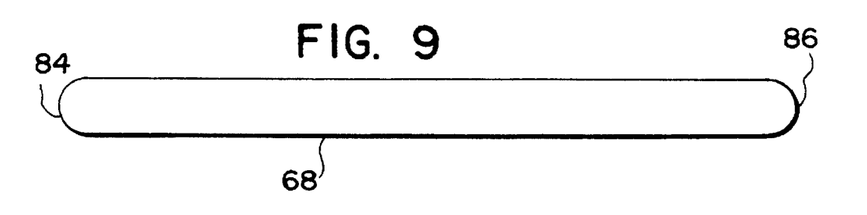
FIG. 9 is a plan view of the flexible supporting band which is secured to the rear laterally extending edge of the lower fabric panel to slightly bow the laterally extending edges of the upper and lower panels upwardly to extend across and just above the upper edge of the eye glasses when the visor is in place thereon.

An elongated flexible supporting band 68 is secured along the inwardly facing surface of the laterally extending edge 24 of the lower layer 10 of the fabric covering 4. The supporting band 68 has a slightly longer lineal dimension than the lineal dimension across the laterally extending edge 24 of the fabric covering 4 whereby the supporting band 68 is slightly flexed when in place between the outer edges 70 and 72 of the pocket 12 at its entrance 14. When so flexed the supporting band 68 is bowed slightly in the upward direction toward the upper layer 6 of the fabric covering 4. The laterally extending edges 24 of the upper and lower fabric panels 6 and 10 of the covering 4 are thereby both bowed slightly in the upward direction. That positions the laterally extending edge 24 of the sun visor in accordance with this invention in a slightly bowed arc along and slightly above the upper edge 74 of the sun glasses 8 when the sun visor is affixed in position thereon. The flexible supporting band 68 bowed slightly in the upward direction along the laterally extending edge 24 thereby keeps the laterally extending edge 24 from drooping down in front of the lens 76 of the sun glasses 8 which would impair vision.

However, the upwardly extending bow of the flexible supporting band 68 is not so great as to raise the intermediate portion 78 of the laterally extending edges 24 so high that there is a significant gap between the upper edge 74 of the sun glasses 8 and the laterally extending edges 24. If the intermediate portion 78 is bowed so much it extends too much above the upper edge 74 of the sun glasses 8, an undesirable arcuate line appears between the tanned and untanned portion of the wearer's forehead.

In a sun visor according to this invention which has a linear dimension of five and one half inches along the laterally extending edges 24 between the outer edges 70 and 72 of the pocket 12 at its entrance 14, a flexible supporting band 68 having a linear dimension of six inches will provide an upwardly extending arc or bow of the right amount to achieve the stated placement of the laterally extending edges 24 of the sun visor relative to the adjacent upper edge 74 of the sun glasses 8 when the sun visor is affixed thereto.

The bow of the flexible band 68 secured to the laterally extending edge 24 of the lower flexible sheet layer 10 of the fabric covering 4 also helps to keep the entrance 14 of the pocket 12 closed tightly enough to prevent items placed therein from inadvertently falling out. The flexible band 68 when bowed upwardly presses the laterally extending edge 24 of the lower panel 10 rather tightly against the laterally extending edge 24 of the upper layer 6 and its inwardly extending flap 26.

In a preferred embodiment, the flexible supporting band 68 has a width of about one-half inch and a thickness of about two hundredths of an inch. The band 68 is preferably made of a light weight strip of relatively stiff plastic material which can be flexed but which springs back to its unflexed original position.

The opaque fabric covering 4 is preferably made of a stretchable fabric material which can be stretched a substantial amount in one direction but very little if any in the direction normal to such one direction. In other words and by way of example, if it can be stretched a substantial amount in the lateral direction it can be stretched very little in the longitudinal direction. Such fabrics are readily available for purchase in stores which sell fabrics. When forming the panels 6 and 10 which make up the covering 4 of the visor, the fabric material is placed so the direction in which it is substantially flexible corresponds with the lateral direction of the visor in which the laterally extending edges 24 extend. Thus when the sun visor is completed in accordance with this invention, the panels 6 and 10 of the fabric covering 4 are substantially stretchable in the lateral direction while being stretchable very little if at all in the longitudinal direction.

Such construction of the fabric covering 4 biases the opposite outer longitudinal edges 80 and 82 of the visor inwardly toward each other when the fabric is in its relaxed or unstretched position. Such inward bias helps to press the first and second connecting strips 36 and 38 which extend from each end of the peripheral frame member 2 more firmly against the corresponding first and second eyeglass cooperative retaining members 46 and 54 to thereby hold the sun visor more securely in place on the sun glasses 8.

The outer ends 84 and 86 of the flexible supporting band 68 are rounded to prevent cutting into the fabric material at each end.

We claim:

1. A sun visor for eye glasses, comprising a sun shade panel member having a first laterally extending edge facing rearwardly, said laterally extending edge extending from a first end thereof to a second end thereof in a straight plane throughout from said first end to said second end, a second peripheral edge extending outwardly from said first end of said first laterally extending edge and around to said second end of said first laterally extending edge, first releasable connecting means extending from said panel member at said first end of said first laterally extending edge to releasably connect to one side of a pair of eye glasses, and second releasable connecting means extending from said panel member at said second end of said first laterally extending edge to releasably connect to the other side of a said pair of eye glasses.

2. A sun visor for eye glasses, comprising a sun shade panel member having a first laterally extending edge facing rearwardly, said laterally extending edge extending from a first end thereof to a second end thereof, a second peripheral edge extending outwardly from said first end of said first laterally extending edge and around to said second end of said first laterally extending edge, first releasable connecting means extending from said panel member at said first end of said first laterally extending edge to releasably connect to one side of a pair of eye glasses, and second releasable connecting means extending from said panel member at said second end of said first laterally extending edge to releasably connect to the other side of a said pair of eye glasses, wherein said sun shade panel member includes a peripheral frame member extending outwardly from said first end of said first laterally extending edge of said panel member and around to said second end of said first laterally extending edge adjacent to said second peripheral edge and in supporting relationship therewith.

3. A sun visor for eye glasses as set forth in claim 2, wherein said sun shade panel member includes a first layer of flexible sheet material facing upwardly when said panel member is releasably connected to said eye glasses and in use, a second layer of flexible sheet material below said first layer and facing downwardly when said panel member is releasably connected to a said pair of eye glasses and in use, said first and second layers of flexible sheet material being joined together around said second peripheral edge of said sun shade panel member.

4. A sun visor for eye glasses as set forth in claim 3, wherein said first and second layers of flexible sheet material comprise an opaque fabric material.

5. A sun visor for eye glasses as set forth in claim 4, wherein said first and second layers of flexible sheet material are joined together around said second peripheral edge by sewing to provide an outermost first peripheral seam, said first and second layers also being joined together by sewing to provide a second peripheral seam spaced apart inwardly of said outermost first peripheral seam, a peripheral through passageway extending around said second peripheral edge of said sun shade panel between said first and second peripheral seams, said peripheral frame member being received in said peripheral through passageway to thereby support said sun shade panel member around its said second peripheral edge.

6. A sun visor for eye glasses as set forth in claim 5, wherein said peripheral through passageway terminates at one end in a first passageway entrance adjacent said first end of said laterally extending edge of said sun shade panel member and terminates at its opposite end in a second passageway entrance adjacent said second end of said laterally extending edge, said peripheral frame member including a first connecting end portion which extends outwardly of said first passageway entrance and a second connecting end portion which extends outwardly of said second passageway entrance, a first releasable connecting member secured to said first connecting end portion of said peripheral frame member, a second releasable connecting member secured to said second connecting end portion of said peripheral frame member, said first connecting end portion and said first releasable connecting member being comprised in said first releasable connecting means, said second connecting end portion and said second releasable connecting member being comprised in said second releasable connecting means.

7. A sun visor for eye glasses as set forth in claim 6 and eye glasses in combination, wherein said first releasable connecting means includes a third releasable connecting member, said third releasable connecting member being releasably connectable to said first releasable connecting member, said third releasable connecting member being securable to said eye glasses on one side thereof, said second releasable connecting means includes a fourth releasable connecting member, said fourth releasable connecting member being releasably connectable to said second releasable connecting member, said fourth releasable connecting member being securable to said eye glasses on the opposite side thereof, said sun shade panel member being releasably connected to said eye glasses when said third and fourth releasable connecting members are secured to said eye glasses and said first releasable connecting member is in releasable securing engagement with said third releasable connecting member and said second releasable connecting member is in releasable securing engagement with said fourth releasable connecting member.

8. A sun visor for eye glasses as set forth in claim 7 and eye glasses in combination, wherein one of said first and third releasable connecting members includes a plurality of tiny flexible hook members extending outwardly therefrom and the other includes a plurality of tiny flexible loop members extending outwardly therefrom, said tiny flexible hook members being releasably connectable to said tiny flexible loop members.

9. A sun visor for eye glasses and eye glasses in combination as set forth in claim 7, wherein one of said second and fourth releasable connecting members includes a plurality of tiny flexible hook members extending outwardly therefrom and the other includes a plurality of tiny flexible loop members extending outwardly therefrom, said tiny flexible hook members being releasably connectable to said tiny flexible loop members.

10. A sun visor for eye glasses as set forth in claim 3, wherein said first and second layers of flexible sheet material joined together around said peripheral edge form a storage pocket, and an entrance to said pocket along said laterally extending edge.

11. A sun visor for eye glasses as set forth in claim 10, wherein said first layer of flexible sheet material includes a laterally extending edge along the upper side of said entrance to said pocket, said second layer of flexible sheet material includes a laterally extending edge along the lower side of said entrance to said pocket, one of said laterally extending edges of said first and second layers of flexible sheet material including a return portion extending inwardly of said pocket to provide a retaining flap to prevent unintended removal of items from said pocket.

12. A sun visor for eye glasses and eye glasses in combination as set forth in claim 7, wherein said eye glasses include a first elongated temple piece hinged thereto on one side by a first hinge member and a second elongated temple piece hinged thereto on the opposite side by a second hinge member, said third releasable connecting member comprising a first sleeve member of flexible stretchable material, a first bore through said first sleeve member to snugly receive said first elongated temple piece therethrough to position and hold said first sleeve member adjacent said first hinge member, said fourth releasable connecting member comprising a second sleeve member of flexible stretchable material, a second bore through said second sleeve member to snugly receive said elongated temple piece therethrough to position and hold said second sleeve member adjacent said second hinge member.

13. A sun visor for eye glasses as set forth in claim 4, wherein said fabric material is stretchable substantially more in one direction than any other, said fabric when comprising the said first and second layers of flexible sheet material of said sun shade panel member being stretchable substantially more in the lateral direction corresponding to the direction in which the said first laterally extending edge of said sun shade panel member extends than in any other direction.

14. A sun visor for eye glasses as set forth in claim 5, wherein said peripheral frame member has a width of about three-sixteenths of an inch and a cross-sectional dimension of about six-hundredths of an inch.

15. A sun visor for eye glasses as set forth in claim 5, wherein said second peripheral seam is spaced apart inwardly of said outermost first peripheral seam a distance of about one-quarter of an inch to provide a peripheral sleeve to receive said peripheral frame member.

16. A sun visor for eye glasses as set forth in claim 3, including an elongated straight band of relatively stiff but flexible material which bows when flexing pressure is applied and springs back to its straight position when such pressure is released, said second layer of flexible sheet material having a laterally extending edge, said elongated straight band being secured to said second layer of flexible sheet material on its upwardly facing surface along its said laterally extending edge.

17. A sun visor for eye glasses as set forth in claim 16, wherein said first layer of flexible sheet material includes a laterally extending edge, said first and second layers joined together at each opposite end of said laterally extending edges, the lineal dimension of said elongated straight but flexible band secured to said upwardly facing surface along said laterally extending edge of said second layer of flexible sheet material being sufficiently longer than the lineal dimension between said opposite ends of said laterally extending edge at which said first and second layers are joined together to require said straight but flexible band to bow slightly when secured in place on said second layer along its said laterally extending edge.

18. A sun visor for eye glasses as set forth in claim 17, wherein said straight but flexible band is bowed in an arc toward said first layer of flexible sheet material to bias said laterally extending edge of said second layer and said band secured thereto against said laterally extending edge of said first layer of flexible sheet material, said first and second layers of flexible sheet material forming a pocket, said laterally extending edges of said first and second layers providing an entrance therebetween into said pocket, said band secured to said laterally extending edge of second layer of flexible sheet material biasing said second layer of flexible sheet material to a pocket closed position against said laterally extending edge of said first layer of flexible sheet material when it is bowed in an arc toward said first layer.

* * * * *